United States Patent
Wenzel et al.

(12)

(10) Patent No.: US 6,245,538 B1
(45) Date of Patent: Jun. 12, 2001

(54) PROCESS FOR RECOVERING CARBOXYLIC ACIDS FROM A FERMENTATION BROTH

(75) Inventors: J. Douglas Wenzel, Cincinnati; Kevin W. Anderson, Indian Springs, both of OH (US)

(73) Assignee: Henkel Corporation, Gulph Mills, PA (US)

( * ) Notice: Subject to any disclaimer, the term of this patent is extended or adjusted under 35 U.S.C. 154(b) by 0 days.

(21) Appl. No.: 09/345,682

(22) Filed: Jun. 30, 1999

Related U.S. Application Data

(62) Division of application No. 08/880,476, filed on Jun. 23, 1997, now Pat. No. 6,143,632, which is a division of application No. 08/704,073, filed on Aug. 28, 1996, now abandoned.

(51) Int. Cl.[7] .................. C12P 7/40; C12P 7/42; C12P 7/44
(52) U.S. Cl. .......... 435/136; 435/142; 435/145; 210/637; 210/639; 210/651; 210/741; 562/580; 562/582

(58) Field of Search ..................... 435/145, 142, 435/134, 136, 254.22; 210/637, 639, 651, 741; 562/580, 582

(56) References Cited

U.S. PATENT DOCUMENTS

| 4,474,882 | * 10/1984 | Kunishige et al. ............. 435/142 |
| 5,254,466 | 10/1993 | Picataggio et al. . |
| 5,648,247 | 7/1997 | Picataggio et al. . |
| 5,962,285 | 10/1999 | Anderson et al. . |

* cited by examiner

Primary Examiner—Herbert J. Lilling
(74) Attorney, Agent, or Firm—John E. Drach; Steven J. Trzaska

(57) ABSTRACT

Carboxylic acids are recovered from a fermentation broth by adjusting the pH of a fermentation broth comprised of a carboxylic acid to at least about 6.0 and then heating the pH-adjusted broth to a temperature sufficient to effect the formation of three immiscible phases, one of which is an oily phase rich in the carboxylic acid.

35 Claims, No Drawings

PROCESS FOR RECOVERING CARBOXYLIC ACIDS FROM A FERMENTATION BROTH

This application is a Div. of Ser. No. 08/880,476 filed Jun. 23, 1997 now U.S. Pat. No. 6,143,532 which is a Div. of Ser. No. 08/704,073 filed Aug. 28, 1996 now abandoned.

BACKGROUND OF THE INVENTION

1. Field of the Invention

This invention relates to a process for recovering a carboxylic acid made by the biological oxidation of a substrate by a microorganism from a fermentation broth.

2. Statement of the Related Art

Standard methods for recovering carboxylic acids in general and polycarboxylic acids in particular from fermentation broths are based on the physical separation of the spent microorganism cells from the aqueous phase such as by centrifugation followed by precipitation of the carboxylic acid as a result of pH reduction of the aqueous phase. This method is unsatisfactory for a number of reasons, the most notable of which include the problem of physically separating the spent cells and then acidifying the cell-free broth to effect the precipitation of the carboxylic acid. The precipitation of the carboxylic acid is time consuming and the separation and isolation of the precipitated carboxylic acid is not always clean.

SUMMARY OF THE INVENTION

The present invention is an improved process for the recovery of a carboxylic acid made by the biological oxidation of a substrate by a microorganism such as a yeast. After employing a standard fermentation procedure to produce a carboxylic acid, the pH of a fermentation broth which contains one or more carboxylic acids is adjusted to a value of at least about 6.0. The pH-adjusted broth is then heated to a temperature sufficient to effect the formation of three immiscible phases. The top phase is a clear, aqueous phase. The middle phase is an oily phase which is rich in the carboxylic acid. The bottom phase is an aqueous phase containing the spent microorganism cells. This method allows the easy isolation of the carboxylic acid by means of a simple phase separation.

Another aspect of the present invention relates to an improved process for making a dicarboxylic acid. This process comprises fermenting a microorganism in a culture medium comprised of a nitrogen source, an organic substrate which is a compound having one carboxyl group and one methyl group or is a compound having one methyl group and a functional group that can be at least partially hydrolyzed to a carboxyl group and a cosubstrate. The substrate is partially neutralized with an alkaline earth metal hydroxide prior to the addition of the substrate to the fermentation broth.

DESCRIPTION OF THE PREFERRED EMBODIMENTS

Other than in the claims and in the operating examples, or where otherwise indicated, all numbers expressing quantities of ingredients or reaction conditions used herein are to be understood as modified in all instances by the term "about".

It is understood that a carboxylic acid is any compound containing one or more carboxyl groups. A polycarboxylic acid is any compound having two or more carboxyl groups.

The process for the recovery of a carboxylic acid according to the invention comprises fermenting a microorganism in a culture medium which is comprised of a nitrogen source, and at least an organic substrate. The organic substrate can be any compound which can be oxidized to a compound having at least one carboxyl group by biooxidation. The microorganism can be any microorganism that is capable of biologically oxidizing an organic substrate as set forth above to a compound having at least one carboxyl group.

The process for the recovery of a carboxylic acid is particularly applicable to the production of polycarboxylic acids by fermentation and most particularly to the production of dicarboxylic acids. In such situations, the substrate can be any compound having at least one methyl group, a terminal carboxyl group and/or a terminal functional group which is oxidizable to a carboxyl group by biooxidation. The substrate can also contain one or more carbon-carbon multiple bonds and/or one or more carbocyclic or heterocyclic aromatic rings. There is an advantage to adding the organic substrate in increments as opposed to an all-in method. In the incremental addition method, the total charge of organic substrate is divided into a plurality of smaller amounts each of which is added to the fermentation broth on a regular basis. The advantage gained by the incremental addition is that the rate of production of carboxylic acid remains essentially constant as opposed to an ever decreasing rate observed with the all-in method. The amount of organic substrate added in each increment and the time between additions will vary depending upon the fermentation conditions, the nature of the substrate, cosubstrate, the microorganism and the carboxylic acid formed in the fermentation. The exact incremental addition parameters can be readily determined by those skilled in the art.

The microorganism can be any microorganism capable of biooxidizing the substrate as defined herein. Typically, such a microorganism will be a yeast. Several strains of yeast are known to excrete alpha, omega-dicarboxylic acids as a byproduct when cultured on alkanes or fatty acids as the carbon source. These strains are set forth in U.S. Pat. No. 5,254,466, the entire contents of which are incorporated herein by reference. Preferably, the microorganism is a beta-oxidation blocked C. tropicalis cell which has been genetically modified so that the chromosomal POX4A, POX4B and both POX5 genes have been disrupted. The substrate flow in this strain is redirected to the omega-oxidation pathway as the result of functional inactivation of the competing β-oxidation pathway by POX gene disruption. The strain may also have one or more reductase genes amplified which results in an increase in the amount of rate-limiting omega-hydroxylase through P450 gene amplification and an increase in the rate of substrate flow through the ω-oxidation pathway. Preferred strains are H5343, AR40 and R24. Strain H5343 has the ATCC accession number ATCC 20962 and is described in U.S. Pat. No. 5,254,466. Strain AR40 is a C. tropicalis cell which is an amplified H 5343 strain wherein all four POX4 genes and both copies of the chromosomal POX5 genes are disrupted by a URA3 selectable marker and which also contains 3 additional copies of the cytochrome P450 gene and 2 additional copies of the reductase gene, the P450RED gene. Strain AR40 has the ATCC accession number ATCC 20987. Strain R24 is an amplified H 5343 strain in which all four POX4 genes and both copies of the chromosomal POX5 genes are disrupted by a URA3 selectable marker and which also contains multiple copies of the reductase gene. Strains AR40 and R24 are described in copending application Ser. No. 07/1975, 154, filed on Nov. 12, 1992, the entire contents of which are incorporated herein by reference.

The first step of the process for the recovery of a carboxylic acid according to the invention is the adjustment of the pH of the fermentation broth to at least 6.0. Typically, the pH value will fall in the range of from 6.0 to 7.5 but may be higher than 7.5 depending upon the fermentation conditions, the nature of the substrate, cosubstrate, the microorganism and the carboxylic acid formed in the fermentation. The optimum pH value will be readily determinable by those skilled in the art. The pH adjustment can take place at any point in the fermentation process.

The second step of the process for the recovery of a carboxylic acid according to the invention involves heating the pH-adjusted fermentation broth to a temperature sufficient to effect the formation of three immiscible phases, one of which is an oily phase rich in the carboxylic acid product. The temperature required to effect the phase separation will typically range in the 60° C.–75° C. range but may be higher than 75° C. depending upon the fermentation conditions, the nature of the substrate, cosubstrate, the microorganism and the carboxylic acid formed in the fermentation. The optimum temperature will be readily determinable by those skilled in the art.

The improved process for making a dicarboxylic acid comprises fermenting a microorganism in a culture medium comprised of a nitrogen source, an organic substrate and a cosubstrate wherein said substrate is a compound having one carboxyl group and one methyl group or is a compound having one methyl group and a functional group that can be at least partially hydrolyzed to a carboxyl group and wherein said substrate is partially neutralized.

The nitrogen source is disclosed in U.S. Pat. No. 5,254,466. The cosubstrate can be any fermentable carbohydrate such as glucose, fructose, maltose, glycerol and sodium acetate. The preferred cosubstrate is glucose, preferably a liquid glucose syrup, for example, 95% dextrose-equivalent syrup, or even lower dextrose-equivalent syrups. Such materials contain small amounts of disaccharides, trisaccharides, and polysaccharides which can be hydrolyzed during the fermentation by the addition of an amylase enzyme.

The organic substrate is any compound having one carboxyl group and one methyl group or is a compound having one methyl group and a functional group that can be at least partially hydrolyzed to a carboxyl group. Thus, the organic substrate can be any aliphatic saturated or unsaturated monocarboxylic acid except formic acid and acrylic acid. The organic substrate can also be an aromatic monocarboxylic acid having a methyl group the simplest example of which is o, m, or p-methyl benzoic acid. The substrate is partially neutralized with an alkaline earth metal hydroxide prior to the addition of the substrate to the fermentation broth. It has been determined that the partial neutralization provides a more rapid induction of dicarboxylic acid production thereby reducing the overall transformation time in the fermentor which ultimately results in improved turn around times in the fermentor and an overall increase in productivity. The optimum degree of partial neutralization will typically vary from 1 to 10% and is preferably from 1% to 2.5% but can be any value from one part per million to 99% depending upon the fermentation conditions, the nature of the substrate, cosubstrate, the microorganism and the carboxylic acid formed in the fermentation will be readily determinable by those skilled in the art. The optimum degree of partial neutralization will be readily determinable by those skilled in the art. The preferred alkaline earth metal hydroxides are calcium and magnesium hydroxide. While the organic substrate will normally be a monocarboxylic acid, it can be any compound having one carboxyl group and one methyl group or having one methyl group and a functional group that can be at least partially hydrolyzed to a carboxyl group thereby permitting at least partial neutralization of the carboxyl group formed in the hydrolysis. Particularly preferred monocarboxylic acids are oleic acid and pelargonic acid.

The use of oleic acid substrates having a high oleic acid content which is defined as those substrates having an oleic acid content of equal to or greater than 90% oleic acid produce a very viscous fermentation broth. Fermentation broths having high viscosities have relatively poor heat transfer and oxygen mass transfer. The use of oleic acid substrates having an oleic acid content of less than 90% result in fermentation broths that are less viscous thereby making the maintenance of proper temperature and dissolved oxygen levels much simpler. An example of such an oleic acid is technical oleic acid the composition of which is set forth in Example 1.

The process according to the invention permits the use of some monocarboxylic acids while avoiding the toxicity problem normally encountered with their use. Some monocarboxylic acids tend to be toxic to some microorganisms, particularly yeasts such as *C. tropicalis* and especially beta-oxidation blocked *C. tropicalis* strains which have been genetically modified so that the chromosomal POX4A, POX4B and both POX5 genes have been disrupted and/or those *C. tropicalis* strains wherein the one or more reductase genes have been amplified. The present invention encompasses the use of a combination of monocarboxylic acids as the organic substrate. The relative amount of each monocarboxylic acid in combination will typically vary from 1/100 to 1/1 with the preferred amount being from 1/1 to 1/10. The amount for any particular fermentation will vary according to the relative toxicities of the monocarboxylic acids and will be readily ascertainable to those skilled in the art.

One advantageous embodiment of the process according to the invention comprises culturing a microorganism in a culture medium comprised of a spent fermentation broth from a preceding fermentation and a fresh fermentation broth comprised of a microorganism, a substrate, a cosubstrate, and a nitrogen source as described above. A spent fermentation broth is a fermentation broth from a previously completed fermentation or a fermentation deemed to be completed and which contains at least the desired product which is either a carboxylic acid and/or a polycarboxylic acid and spent microorganism cells. The optimum amount of spent fermentation broth used as a heel will typically range from 5% to 10% by weight but can be any value amount of material from a previous fermentation used as a heel will typically range from 1% to 99% by weight of the total charge depending upon the fermentation conditions, the nature of the substrate, cosubstrate, the microorganism and the carboxylic acid formed in the fermentation will be readily determinable by those skilled in the art. The optimum amount of material used in any particular fermentation will be readily determinable by those skilled in the art.

The following examples are meant to illustrate but not to limit the invention.

EXAMPLE 1

Method For Separating a Dicarboxylic Acid

A fermentor was charged with a semi-synthetic growth medium having the composition 70 g/l glucose (anhydrous), 6.7 g/l Yeast Nitrogen Base (Difco Laboratories), 3 g/l yeast extract, 3 g/l ammonium sulfate, 2 g/l monopotassium phosphate, and 0.04 g/l ferrous sulfate. Components were made as concentrated solutions for autoclaving then added to the fermentor upon cooling: final pH approximately 5.2. This charge was inoculated with 5–10% of an overnight culture of *C. tropicalis* H5343 prepared in YM medium (Difco Laboratories) as described in the methods of Examples 17 and 20 of U.S. Pat. No. 5,254,466. Cells were then cultivated to about 15–35 g dry weight/l limited by the available nitrogen in the medium. There was a slight stoichiometric excess amount of glucose in the above charge that remained for about 1–3 hours after depletion of nitrogen sources. Air and agitation were supplied to maintain the dissolved oxygen at greater than about 40% of saturation versus air. Lower dissolved oxygen resulted in substantial in situ accumulation of partial glucose-catabolic products, primarily ethanol. The pH was maintained at about 5N by the addition of 5N KOH. About 200 g of technical grade oleic acid having the following composition: 0.30% $C_{12}$; 2.4% $C_{14}$; 0.60% $C_{14:1}$; 4.7% $C_{16}$; 4.6% $C_{16:1}$; 0.20% $C_{17}$; 0.80$C_{18}$; 69.9% $C_{18:1}$; 10.50% $C_{18:2}$; 0.30% $C_{18:3}$ saponified with calcium hydroxide was added and the glucose cosubstrate feed (1.8 g/l/hr) is started near the time the culture enters stationary phase to initiate omega oxidation. Two successive charges of 250 g of technical grade oleic acid saponified with calcium hydroxide were added. The first 250 g charge was added about 23 hours after the initial 200 g charge, and the second 250 g charge was added about 23 hours after the first 250 g charge. After the second addition, the pH was raised to 6.0 with KOH and maintained at 6.0 for the rest of the fermentation. The fermentation was continued until GLC analysis showed an oleic acid content of less than 1 g/Kg at which time the fermentation broth was placed in a 70°C. oven. The broth separated into three immiscible phases. The top phase was a clear, aqueous phase. The middle phase was an oily phase which is rich in the 9-octadecenedioic acid. The bottom phase was an aqueous phase containing the spent microorganism cells. The final whole broth from the fermentor (all three phases mixed, homogenous) contained 37.4 g/Kg of 9-octadecenedioic acid. The same broth allowed to separate into three immiscible phases as previously described contained 0.3 g/Kg of 9-octadecenedioic acid in the top aqueous phase and about 92 g/Kg of 9-octadecenedioic acid in the oily middle phase. Dibasic acids were quantified by extracting the whole fermentation broth, methylesterifying the extract, and analyzing for dibasic acid methylesters by GLC using an HP-lnnowax capillary column.

EXAMPLE 2

Comparative Example

The method of Example 1 was repeated except that the oleic feed in two charges of 500 g each, NaOH was used for the pH adjustment and the final pH was 5.03. No phase separation occurred. The final whole broth from the fermentor contained 22.2 g/Kg of 9-octadecenedioic acid. The method for quantitating dibasic acid was the same as in Example 1.

What is claimed is:

1. An improved process for making a dicarboxylic acid which comprises fermenting a microorganism in a culture medium comprised of a nitrogen source, a substrate and a cosubstrate wherein said substrate is a compound having one carboxyl group and one methyl group or is a compound having one methyl group and a functional group that can be at least partially hydrolyzed to a carboxyl group and wherein said substrate is partially neutralized prior to its addition to the culture medium.

2. The process of claim 1 wherein said microorganism is a beta-oxidation blocked *C. tropicalis* cell wherein both copies of the chromosomal POX5 gene and the chromosomal POX4A and POX4B genes are disrupted.

3. The process of claim 1 wherein said substrate is a monocarboxylic acid.

4. The process of claim 3 wherein said monocarboxylic acid is oleic acid.

5. The process of claim 1 wherein said microorganism is *C. tropicalis* strain H5343.

6. The process of claim 3 wherein said substrate is a combination of pelargonic acid and oleic acid.

7. An improved process for making a dicarboxylic acid comprising the steps of: (1) fermenting a microorganism in a culture medium comprised of a nitrogen source, an organic substrate and a cosubstrate wherein said substrate is a compound having one carboxyl group and one methyl group or is a compound having one methyl group and a functional group that can be at least partially hydrolyzed to a carboxyl group and wherein said substrate is partially neutralized with an alkaline earth metal hydroxide prior to its addition to the culture medium; (2) adjusting the pH of said culture medium of step (1) to at least about 6.0; (3) heating the culture medium of step (2) to a temperature sufficient to effect the formation of three immiscible phases, one of which is an oily phase rich in said 9-octadecenedioic acid.

8. The process of claim 7 wherein said pH is from about 6.0 to about 7.5.

9. The process of claim 7 wherein said temperature is from about 60° C. to about 75° C.

10. The process of claim 7 wherein said substrate is a carboxylic acid.

11. The process of claim 10 wherein said carboxylic acid is oleic acid.

12. The process of claim 7 wherein said substrate is technical oleic acid having an oleic acid content of less than 90% by weight.

13. The process of claim 7 wherein said dicarboxylic acid is 9-octadecenedioic acid.

14. The process of claim 7 wherein said substrate is a combination of pelargonic acid and oleic acid.

15. The process of claim 7 wherein said microorganism is a beta-oxidation blocked *C. tropicalis* cell wherein both copies of the chromosomal POX5 gene and the chromosomal POX4A and POX4B genes are disrupted.

16. The process of claim 14 wherein said microorganism is *C. tropicalis* strain H5343.

17. An improved process for making 9-octadecenedioic acid comprising the steps of: (1) fermenting *C. tropicalis* strain H5343 in a culture medium comprised of a nitrogen source, oleic acid partially neutralized with an alkaline earth metal hydroxide prior to its addition to the culture medium and a cosubstrate; (2) adjusting the pH of said culture medium of step (1) to at least about 6.0; (3) heating the culture medium of step (2) to a temperature sufficient to effect the formation of three immiscible phases, one of which is an oily phase rich in said 9-octadecenedioic acid.

18. The process of claim 17 wherein said pH is from about 6.0 to about 7.5.

19. The process of claim 17 wherein said temperature is from about 60° C. to about 75° C.

20. The process of claim 17 wherein said substrate is technical oleic acid having an oleic acid content of less than 90% by weight.

21. An improved process for making a dicarboxylic acid comprising the steps of: (1) fermenting a microorganism in a culture medium comprised of a spent fermentation broth, a nitrogen source, an organic substrate and a cosubstrate wherein said substrate is a compound having one carboxyl group and one methyl group or is a compound having one methyl group and a functional group that can be at least partially hydrolyzed to a carboxyl group and wherein said substrate is partially neutralized with an alkaline earth metal hydroxide prior to its addition to the culture medium; (2) adjusting the pH of a fermentation broth comprised of a carboxylic acid to at least about 6.0; (3) heating the broth from step (2) to a temperature sufficient to effect the formation of three immiscible phases, one of which is an oily phase rich in said carboxylic acid.

22. The process of claim 21 wherein said pH is from about 6.0 to about 7.5.

23. The process of claim 21 wherein said temperature is from about 60° C. to about 75° C.

24. The process of claim 21 wherein said substrate is a carboxylic acid.

25. The process of claim 24 wherein said carboxylic acid is oleic acid.

26. The process of claim 21 wherein said substrate is technical oleic acid having an oleic acid content of less than 90% by weight.

27. The process of claim 21 wherein said dicarboxylic acid is 9-octadecenedioic acid.

28. The process of claim 21 wherein said substrate is a combination of pelargonic acid and oleic acid.

29. The process of claim 21 wherein said microorganism is a beta-oxidation blocked *C. tropicalis* cell wherein both copies of the chromosomal POX5 gene and the chromosomal POX4A and POX4B genes are disrupted.

30. An improved process for making a dicarboxylic acid which comprises: (1) forming a culture medium comprised of a nitrogen source, a portion of the required amount of a substrate and a cosubstrate wherein said substrate is compound having one carboxyl group and one methyl group or is a compound having one methyl group and a functional group that can be at least partially hydrolyzed to a carboxyl group and wherein said substrate is partially neutralized prior to its addition to the culture medium; (2) fermenting a microorganism in the presence of said culture medium while adding the remaining portion of said substrate in increments.

31. The process of claim 30 wherein said microorganism is a beta-oxidation blocked *C. tropicalis* cell wherein both copies of the chromosomal POX5 gene and the chromosomal POX4A and POX4B genes are disrupted.

32. The process of claim 30 wherein said substrate is a monocarboxylic acid.

33. The process of claim 32 wherein said monocarboxylic acid is oleic acid.

34. The process of claim 21 wherein said microorganism is *C. tropicalis* strain H5343.

35. The process of claim 30 wherein said substrate is a combination of pelargonic acid and oleic acid.

* * * * *